United States Patent
Fellers et al.

(10) Patent No.: US 10,633,671 B2
(45) Date of Patent: Apr. 28, 2020

(54) PLANT GERMPLASM RESISTANT TO RNA VIRUSES

(71) Applicants: The United States of America, as represented by the Secretary of Agriculture, Washington, DC (US); Kansas State University Research Foundation, Manhattan, KS (US)

(72) Inventors: John Fellers, Manhattan, KS (US); Harold N. Trick, Olsburg, KS (US); Luisa Cruz, Plant City, FL (US); Jessica Rupp, Manhattan, KS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 125 days.

(21) Appl. No.: 15/875,168

(22) Filed: Jan. 19, 2018

(65) Prior Publication Data

US 2018/0148736 A1 May 31, 2018

Related U.S. Application Data

(62) Division of application No. 14/494,661, filed on Sep. 24, 2014, now Pat. No. 9,909,139.

(60) Provisional application No. 61/882,116, filed on Sep. 25, 2013.

(51) Int. Cl.
*C12N 15/82* (2006.01)
*C07K 14/415* (2006.01)

(52) U.S. Cl.
CPC ........ *C12N 15/8283* (2013.01); *C07K 14/415* (2013.01); *C12N 15/8218* (2013.01)

(58) Field of Classification Search
None
See application file for complete search history.

(56) References Cited

U.S. PATENT DOCUMENTS 7,772,462 B2 * 8/2010 Jahn .................. C12N 15/8283
800/278

OTHER PUBLICATIONS

Sequence Accession EF190330, sequence alignment provided at the end of the office action (Year: 2007).*
Sequence Accession B44452, Jun. 10, 1993, attached to Office Action.
Sequence Accession M95818, Apr. 27, 1993, attached to Office Action.

* cited by examiner

*Primary Examiner* — Elizabeth F McElwain
(74) *Attorney, Agent, or Firm* — John Fado; Ariel Atkinson

(57) ABSTRACT

Disclosed is a dsRNA construct used to silencing specific eukaryotic translation initiation factor in plants to produce a plant resistant to viruses such as Potyviruses, Luteoviruses, and Furoviruses. More specifically, the plant would be resistant to viruses such as Wheat streak mosaic virus, *Triticum* mosaic virus, Soil bourne mosaic virus, or Barley yellow dwarf virus. Also disclosed are non-transgenic wheat plants having the genes for eIF(iso)4E-2 or eIF4G silenced.

Figure 1A:
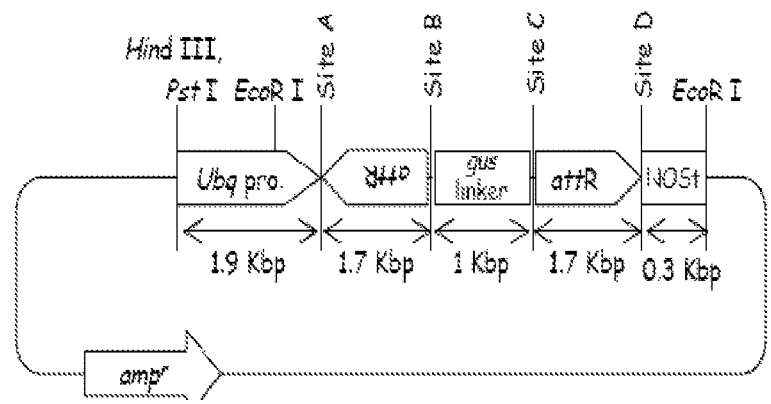

12 Claims, 1 Drawing Sheet
Specification includes a Sequence Listing.

SEQUENCE LISTING

<160> NUMBER OF SEQ ID NOS: 8

<210> SEQ ID NO 1
<211> LENGTH: 630
<212> TYPE: DNA
<213> ORGANISM: Triticum aestivum

<400> SEQUENCE: 1

```
atggcagagg tcgaagctgc gctcccggtg gcggcgacag agaccccgga ggtcgccgcc      60
gagggcgacg cgggtgcggc cgaggcgaag gggccgcaca agctgcagcg gcagtggacc     120
ttctggtacg acatccagac caagcccaag cccggcgccg cctgggcac ctcgctcaaa      180
```

```
aagggctaca ccttcgacac cgtcgaagag ttctggtgct tgtatgatca gattttccgt    240
ccgagtaagc tggtaggaag tgctgatttt catttattca aggctggggt agaaccaaag    300
tgggaagatc cagagtgcgc aaatggaggc aaatggactg tgatatctag caggaagacc    360
aatcttgata ccatgtggct tgaaacgtgt atggctctga ttggagagca gttcgatgaa    420
agccaggaaa tttgtggtgt tgttgctagt gtccgccaga gacaggataa gctttcatta    480
tggactaaga ctgccagtaa cgaagctgtt caggtggaca ttggcaagaa atggaaggag    540
gttattgact acaatgataa gatggtctac agcttccacg atgactcaag aagtcagaaa    600
ccaagcagag gtggacgata caccgtctaa                                     630
```

<210> SEQ ID NO 2
<211> LENGTH: 209
<212> TYPE: PRT
<213> ORGANISM: Triticum aestivum

<400> SEQUENCE: 2

```
Met Ala Glu Val Glu Ala Ala Leu Pro Val Ala Ala Thr Glu Thr Pro
1               5                   10                  15

Glu Val Ala Ala Glu Gly Asp Ala Gly Ala Ala Glu Ala Lys Gly Pro
            20                  25                  30

His Lys Leu Gln Arg Gln Trp Thr Phe Trp Tyr Asp Ile Gln Thr Lys
        35                  40                  45

Pro Lys Pro Gly Ala Ala Trp Gly Thr Ser Leu Lys Lys Gly Tyr Thr
    50                  55                  60

Phe Asp Thr Val Glu Glu Phe Trp Cys Leu Tyr Asp Gln Ile Phe Arg
65                  70                  75                  80

Pro Ser Lys Leu Val Gly Ser Ala Asp Phe His Leu Phe Lys Ala Gly
                85                  90                  95

Val Glu Pro Lys Trp Glu Asp Pro Glu Cys Ala Asn Gly Gly Lys Trp
            100                 105                 110

Thr Val Ile Ser Ser Arg Lys Thr Asn Leu Asp Thr Met Trp Leu Glu
        115                 120                 125

Thr Cys Met Ala Leu Ile Gly Glu Gln Phe Asp Glu Ser Gln Glu Ile
    130                 135                 140

Cys Gly Val Val Ala Ser Val Arg Gln Arg Gln Asp Lys Leu Ser Leu
145                 150                 155                 160

Trp Thr Lys Thr Ala Ser Asn Glu Ala Val Gln Val Asp Ile Gly Lys
                165                 170                 175

Lys Trp Lys Glu Val Ile Asp Tyr Asn Asp Lys Met Val Tyr Ser Phe
            180                 185                 190

His Asp Asp Ser Arg Ser Gln Lys Pro Ser Arg Gly Gly Arg Tyr Thr
        195                 200                 205

Val
```

<210> SEQ ID NO 3
<211> LENGTH: 4467
<212> TYPE: DNA
<213> ORGANISM: Triticum aestivum
<220> FEATURE:
<221> NAME/KEY: misc_feature
<222> LOCATION: (3222)..(3222)
<223> OTHER INFORMATION: n is a, c, g, or t

<400> SEQUENCE: 3

```
atggggcatc aaggacaaac catgatgtat ccgtctgttg ctcatccaat ccctcctcaa    60
```

```
ctgggcaatg ttaatttgaa catggcttca cagtatcctc agcaacagca gaataagctt      120
gttgctcctc gaaagagcag taatatcaaa attactgatc caaacactaa caagaagtg       180 gttcttgggc ggccttcacc taatgtagca gtacaaccgc agcaagtcag tggtgttgca      240
actcagccta tggtttacta tactaatcca cagcagacct cgtataacca gtcaggcacg      300
tattactccg gcactgctgg tgttgttccc actggatcac agggcaggtt tggttatcct      360
gccactcaag ctggtcaatc aattcctttc atgaaccctt ctatgtcaaa tactgttcct      420
gccagccaca aggacaacat agctgggcct gcaccatctg gtcagtccca actcataggc      480
aaaccacaag gtgggttgca catggagaaa cctgttccct cggtcaagat aagtatgcct      540
gcaggtagat cagacgcttc taaattcggg gtcgctgacc atgcggtaca acatcgacaa      600
aaggataatg aagttatttc tggtgctatg gtttcgaata aaccagttag tgagaaggag      660
agcaaggcac catctatccc agagaagcac tccaaggaaa gtaaagcacc atctgccgtg      720
gagaagcatc ccactgcggt gactcaacct ttaccgattc aagctgcaaa gccagaaact      780
gatgcagcga ctgcaaattc accctcattc ttgaccggag ctgatgaaaa gaagaatcc       840 cttccaatga ctgattcact taaggataac aagaaaaatg caactagaaa tgacacaaag      900
aatttgccgc aacaacctca gtctgcttcc cctgccgaag agttgaaggg gcaaacttct      960
gtgaagcttg gtgatgatgt ggttggtcac atggaaacca agagcttcga tagtgaaaag     1020
gtggatttaa ccagcaaggt ttcaggctta acatcagcaa catctgaaag tagtatttct     1080
cctattcttg gtaaaagtga agctgacagc acatcagtag atgctgctga tgttcctgcc     1140
atggtaatca gctctgcaaa attgtcctct gcgagcactg gggagcccca agcagtagaa     1200
agcttaggtg ttgctgctgt taaatctaag gagattgaaa taactcacca aatttcacct     1260
gaatctagtg atggcaaaat tatgtctgat tctactgaaa atgaatcaca tgacttcacg     1320
gtggacttgg ctgagcaggc atcattggca acttcaaagc ctggtaattc agatgcaaca     1380
tcttttgtaa ctgacccgca agagctaccc aaggagtgca acatctgt accggaggac       1440 cacagtttga tgaatacatc acataataag gatacccaaa ctttatcagc ttctgtggat     1500
gccagcgatg tgtctgaggt caattctgga acctcatcag agtctaccag ccaaagtacc     1560
aacgataaag atatcagaag tagcattcag gaaactggat tagctgtttc tggtattact     1620
cctggcatgt tgcctgtgaa tcattcagtt gcatctgagg ggcaagtcaa acatgcagat     1680
ggagcgaagg atgagtctag tactgagcaa tcaagtgccg taccaacagg ttctgttaga     1740
cccttatcaa gggaaaaacc tactgcagag cttgcccgaa caaagtctac agctgggaga     1800
aagaagaaac ggaaggaaat gctttcaaaa gctgatgctg ctgggagctc agatctgtac     1860
aatgcataca aaggaccaca agaacagtct gagagtgttg ccacatcaga cggtgctgat     1920
agttcttcaa cagtcgacgg gacacatgtg ctgcctgagg aatcagaaag ggaggtgatg     1980
tgtgaggacg atgaaagaa aaagttgag ccggatgatt gggaagatgc agcagacatg       2040
tctactccaa agctgcaaag ttcggactct ggaaaccagg ctagtgcagt tcaattgcca     2100
gattctgata tgactgaagc taatggccga aagaaatatt ctcgtgattt tcttctaact     2160
tttgcacatc agtattctag tcttcctgtt ggcatccgga tggatactgt cactagtacg     2220
ctattcaaag atttggcagg aaaatcctat gttattgatc gggaacctca cccaagttct     2280
gcaaggggat ctgatagacc aacatctcgc ggtgatcgcc gtggtcctgc tatggatgat     2340
gataagtggt taaaatcagg tgttccttac agtcctaacc gtgatgccca catggacttg     2400
```

| | |
|---|---|
| acaaacggcc cagcaattaa ttaccgtggc ggcccaggag gcgctcatgg tgttctgagg | 2460 |
| aatccacgtg gtgcactcct tgtgggacca caatccaatg ctcctcaagt accccgcagt | 2520 |
| ggctctgatg cagatagatg cagcaaaag gtctgatcc catctcctgt tacacccatg | 2580 |
| caagtaatgc acaaagccga gaaaagtat gttgtcggca agtttctga tgaggagcag | 2640 |
| gcaaagcaga ggcagctgaa agccattctg aataaactga ccccacaaaa ctttgacaag | 2700 |
| cttttttgaac aagtgaaaga ggtgaacatt gacaatgtat caactcttac tggggtgatt | 2760 |
| tcacagatat ttgacaaagc tttgatggaa ccaactttct gtgaaatgta tgccaacttc | 2820 |
| tgttcccatt tggctggtgc cctgccagac tttagtgagg acaatgaaaa gattacattc | 2880 |
| aagagactgc tattgaacaa gtgccaagag gagtttgaga ggggagaaag agaagaagct | 2940 |
| gaagcagata aaacggagga ggaaggtgag attaagcaaa cgaaagagga agggaagaa | 3000 |
| aagagagtta aagctcgaag gcgcatgctg ggtaatatta gattgattgg agaattgtac | 3060 |
| aaaaagagga tgttgacaga gcgcatcatg catgaatgca tcaaaaaatt gttgggaaat | 3120 |
| tatcagaatc cagatgagga gaacattgaa gcactatgca aattgatgag tacaattgga | 3180 |
| gagatgatag atcatcccaa ggctaaggaa catatggatg cntatttga tagaatgcgc | 3240 |
| aacctgtcga ccagtcaact gatatcttcc cgtgttagat tcctgctcag agattcaatc | 3300 |
| gatctcagga agaacaaatg gcagcaaagg cgtaaagtgg atggccccaa gaagattgat | 3360 |
| gaggttcaca gggatgcagc tcaggaaaga catgctcaat cgagtaggtc tcgtggtcca | 3420 |
| gtcgttagtt ctcttccaag aagagggca ccctctatgg attacggctc ccgtggctca | 3480 |
| gcagcaccat tggtatctcc aggtcctcag caacgagggc gtggatttgg taatcaagat | 3540 |
| attcggtatg agcaggaaag gcatcagttt gatagaactg ttcccttcc ccagcgttct | 3600 |
| gtaaaggacg aagctatcac tcttggacca caaggtggcc tagctagggg tatgtcttta | 3660 |
| agagggcagc caccggtatc aaattctgaa cttcctagtg ttgttgacca gcgcaggatt | 3720 |
| gtatctggtc ctaatgggta caattctgtg ccttcaacaa caagagaaga cactagctct | 3780 |
| agaattccag atcgattttc tgggagaata gcacctgctg cacaatctgc tagttcttca | 3840 |
| cacagacctg ccagccagga gggtcgttca ggaaataaat catactctga ggaggaattg | 3900 |
| agagagaaat ctattgcaac catccgggaa tattatagtg cgaaagatga aaggaagtt | 3960 |
| gcattgtgta ttgaggagtt gaatgctccg agcttctatc cttctcttgt atcactttgg | 4020 |
| gtaaatgatt cctttgagag gaaagatatg gaaagagagt tgttggcaaa gctctttgtc | 4080 |
| gggctttaca atggtggata taatttattg agcaagcctc agctcattga ggggctttca | 4140 |
| tccgttcttg cttcattgga ggatgctcta agtgattctc caagagcggc agagtatctt | 4200 |
| ggacgtcttc ttgcaaggtt tgtggtggag aagatactgg ttttgcaaga cgtaggtaaa | 4260 |
| ttgattgaag aaggcggaga ggagcctgga caccttgtgc aggaaggcat cgcagctgat | 4320 |
| gtccttggcg cagtcttgga gtggatcaga acagaaaagg gggattcctt cttgaaggag | 4380 |
| gccaagacaa gctccaatct caagttggag gatttcagac cgcagcatct taagaggtca | 4440 |
| aagttggatg ccttcatgtt gacttaa | 4467 |

<210> SEQ ID NO 4
<211> LENGTH: 1488
<212> TYPE: PRT
<213> ORGANISM: Triticum aestivum

<400> SEQUENCE: 4

Met Gly His Gln Gly Gln Thr Met Met Tyr Pro Ser Val Ala His Pro

```
1               5                   10                  15
Ile Pro Pro Gln Leu Gly Asn Val Asn Leu Asn Met Ala Ser Gln Tyr
                20                  25                  30
Pro Gln Gln Gln Gln Asn Lys Leu Val Ala Pro Arg Lys Ser Ser Asn
                35                  40                  45
Ile Lys Ile Thr Asp Pro Asn Thr Asn Lys Glu Val Val Leu Gly Arg
 50                  55                  60
Pro Ser Pro Asn Val Ala Val Gln Pro Gln Gln Val Ser Gly Val Ala
 65                  70                  75                  80
Thr Gln Pro Met Val Tyr Tyr Thr Asn Pro Gln Gln Thr Ser Tyr Asn
                85                  90                  95
Gln Ser Gly Thr Tyr Tyr Ser Gly Thr Ala Gly Val Val Pro Thr Gly
                100                 105                 110
Ser Gln Gly Arg Phe Gly Tyr Pro Ala Thr Gln Ala Gly Gln Ser Ile
                115                 120                 125
Pro Phe Met Asn Pro Ser Met Ser Asn Thr Val Pro Ala Ser His Lys
                130                 135                 140
Asp Asn Ile Ala Gly Pro Ala Pro Ser Gly Gln Ser Gln Leu Ile Gly
145                 150                 155                 160
Lys Pro Gln Gly Gly Leu His Met Glu Lys Pro Val Pro Ser Val Lys
                165                 170                 175
Ile Ser Met Pro Ala Gly Arg Ser Asp Ala Ser Lys Phe Gly Val Ala
                180                 185                 190
Asp His Ala Val Gln His Arg Gln Lys Asp Asn Glu Val Ile Ser Gly
                195                 200                 205
Ala Met Val Ser Asn Lys Pro Val Ser Glu Lys Glu Ser Lys Ala Pro
210                 215                 220
Ser Ile Pro Glu Lys His Ser Lys Glu Ser Lys Ala Pro Ser Ala Val
225                 230                 235                 240
Glu Lys His Pro Thr Ala Val Thr Gln Pro Leu Pro Ile Gln Ala Ala
                245                 250                 255
Lys Pro Glu Thr Asp Ala Ala Thr Ala Asn Ser Pro Ser Phe Leu Thr
                260                 265                 270
Gly Ala Asp Glu Lys Lys Glu Ser Leu Pro Met Thr Asp Ser Leu Lys
                275                 280                 285
Asp Asn Lys Lys Asn Ala Thr Arg Asn Asp Thr Lys Asn Leu Pro Gln
                290                 295                 300
Gln Pro Gln Ser Ala Ser Pro Ala Glu Glu Leu Lys Gly Gln Thr Ser
305                 310                 315                 320
Val Lys Leu Gly Asp Asp Val Val Gly His Met Glu Thr Lys Ser Phe
                325                 330                 335
Asp Ser Glu Lys Val Asp Leu Thr Ser Lys Val Ser Gly Leu Thr Ser
                340                 345                 350
Ala Thr Ser Glu Ser Ser Ile Ser Pro Ile Leu Gly Lys Ser Glu Ala
                355                 360                 365
Asp Ser Thr Ser Val Asp Ala Ala Asp Val Pro Ala Met Val Ile Ser
                370                 375                 380
Ser Ala Lys Leu Ser Ser Ala Ser Thr Gly Glu Pro Gln Ala Val Glu
385                 390                 395                 400
Ser Leu Gly Val Ala Ala Val Lys Ser Lys Glu Ile Glu Ile Thr His
                405                 410                 415
Gln Ile Ser Pro Glu Ser Ser Asp Gly Lys Ile Met Ser Asp Ser Thr
                420                 425                 430
```

```
Glu Asn Glu Ser His Asp Phe Thr Val Asp Leu Ala Glu Gln Ala Ser
            435                 440                 445

Leu Ala Thr Ser Lys Pro Gly Asn Ser Asp Ala Thr Ser Phe Val Thr
    450                 455                 460

Asp Pro Gln Glu Leu Pro Lys Glu Cys Thr Thr Ser Val Pro Glu Asp
465                 470                 475                 480

His Ser Leu Met Asn Thr Ser His Asn Lys Asp Thr Gln Thr Leu Ser
                485                 490                 495

Ala Ser Val Asp Ala Ser Asp Val Ser Glu Val Asn Ser Gly Thr Ser
            500                 505                 510

Ser Glu Ser Thr Ser Gln Ser Thr Asn Asp Lys Asp Ile Arg Ser Ser
            515                 520                 525

Ile Gln Glu Thr Gly Leu Ala Val Ser Gly Ile Thr Pro Gly Met Leu
            530                 535                 540

Pro Val Asn His Ser Val Ala Ser Glu Gly Gln Val Lys His Ala Asp
545                 550                 555                 560

Gly Ala Lys Asp Glu Ser Ser Thr Glu Gln Ser Ser Ala Val Pro Thr
                565                 570                 575

Gly Ser Val Arg Pro Leu Ser Arg Glu Lys Pro Thr Ala Glu Leu Ala
            580                 585                 590

Arg Thr Lys Ser Thr Ala Gly Arg Lys Lys Arg Lys Glu Met Leu
            595                 600                 605

Ser Lys Ala Asp Ala Ala Gly Ser Ser Asp Leu Tyr Asn Ala Tyr Lys
            610                 615                 620

Gly Pro Gln Glu Gln Ser Glu Ser Val Ala Thr Ser Asp Gly Ala Asp
625                 630                 635                 640

Ser Ser Ser Thr Val Asp Gly Thr His Val Leu Pro Glu Glu Ser Glu
                645                 650                 655

Arg Glu Val Met Cys Glu Asp Asp Gly Lys Lys Lys Val Glu Pro Asp
            660                 665                 670

Asp Trp Glu Asp Ala Ala Asp Met Ser Thr Pro Lys Leu Gln Ser Ser
            675                 680                 685

Asp Ser Gly Asn Gln Ala Ser Ala Val Gln Leu Pro Asp Ser Asp Met
            690                 695                 700

Thr Glu Ala Asn Gly Arg Lys Lys Tyr Ser Arg Asp Phe Leu Leu Thr
705                 710                 715                 720

Phe Ala His Gln Tyr Ser Ser Leu Pro Val Gly Ile Arg Met Asp Thr
                725                 730                 735

Val Thr Ser Thr Leu Phe Lys Asp Leu Ala Gly Lys Ser Tyr Val Ile
            740                 745                 750

Asp Arg Glu Pro His Pro Ser Ser Ala Arg Gly Ser Asp Arg Pro Thr
            755                 760                 765

Ser Arg Gly Asp Arg Arg Gly Pro Ala Met Asp Asp Lys Trp Leu
            770                 775                 780

Lys Ser Gly Val Pro Tyr Ser Pro Asn Arg Asp Ala His Met Asp Leu
785                 790                 795                 800

Thr Asn Gly Pro Ala Ile Asn Tyr Arg Gly Gly Pro Gly Gly Ala His
                805                 810                 815

Gly Val Leu Arg Asn Pro Arg Gly Ala Leu Leu Val Gly Pro Gln Ser
            820                 825                 830

Asn Ala Pro Gln Val Pro Arg Ser Gly Ser Asp Ala Asp Arg Trp Gln
            835                 840                 845
```

```
Gln Lys Gly Leu Ile Pro Ser Pro Val Thr Pro Met Gln Val Met His
850                 855                 860

Lys Ala Glu Lys Lys Tyr Val Gly Lys Val Ser Asp Glu Gln
865                 870                 875                 880

Ala Lys Gln Arg Gln Leu Lys Ala Ile Leu Asn Lys Leu Thr Pro Gln
                885                 890                 895

Asn Phe Asp Lys Leu Phe Glu Gln Val Lys Glu Val Asn Ile Asp Asn
                900                 905                 910

Val Ser Thr Leu Thr Gly Val Ile Ser Gln Ile Phe Asp Lys Ala Leu
            915                 920                 925

Met Glu Pro Thr Phe Cys Glu Met Tyr Ala Asn Phe Cys Ser His Leu
930                 935                 940

Ala Gly Ala Leu Pro Asp Phe Ser Glu Asp Asn Glu Lys Ile Thr Phe
945                 950                 955                 960

Lys Arg Leu Leu Leu Asn Lys Cys Gln Glu Glu Phe Glu Arg Gly Glu
                965                 970                 975

Arg Glu Glu Ala Glu Ala Asp Lys Thr Glu Glu Glu Gly Glu Ile Lys
                980                 985                 990

Gln Thr Lys Glu Glu Arg Glu Glu Lys Arg Val Lys Ala Arg Arg Arg
            995                 1000                1005

Met Leu Gly Asn Ile Arg Leu Ile Gly Glu Leu Tyr Lys Lys Arg
    1010                1015                1020

Met Leu Thr Glu Arg Ile Met His Glu Cys Ile Lys Lys Leu Leu
    1025                1030                1035

Gly Asn Tyr Gln Asn Pro Asp Glu Glu Asn Ile Glu Ala Leu Cys
    1040                1045                1050

Lys Leu Met Ser Thr Ile Gly Glu Met Ile Asp His Pro Lys Ala
    1055                1060                1065

Lys Glu His Met Asp Ala Tyr Phe Asp Arg Met Arg Asn Leu Ser
    1070                1075                1080

Thr Ser Gln Leu Ile Ser Ser Arg Val Arg Phe Leu Leu Arg Asp
    1085                1090                1095

Ser Ile Asp Leu Arg Lys Asn Lys Trp Gln Gln Arg Arg Lys Val
    1100                1105                1110

Asp Gly Pro Lys Lys Ile Asp Glu Val His Arg Asp Ala Ala Gln
    1115                1120                1125

Glu Arg His Ala Gln Ser Ser Arg Ser Arg Gly Pro Val Val Ser
    1130                1135                1140

Ser Leu Pro Arg Arg Gly Ala Pro Ser Met Asp Tyr Gly Ser Arg
    1145                1150                1155

Gly Ser Ala Ala Pro Leu Val Ser Pro Gly Pro Gln Gln Arg Gly
    1160                1165                1170

Arg Gly Phe Gly Asn Gln Asp Ile Arg Tyr Glu Gln Glu Arg His
    1175                1180                1185

Gln Phe Asp Arg Thr Val Pro Leu Pro Gln Arg Ser Val Lys Asp
    1190                1195                1200

Glu Ala Ile Thr Leu Gly Pro Gln Gly Gly Leu Ala Arg Gly Met
    1205                1210                1215

Ser Leu Arg Gly Gln Pro Pro Val Ser Asn Ser Glu Leu Pro Ser
    1220                1225                1230

Val Val Asp Gln Arg Arg Ile Val Ser Gly Pro Asn Gly Tyr Asn
    1235                1240                1245

Ser Val Pro Ser Thr Thr Arg Glu Asp Thr Ser Ser Arg Ile Pro
```

```
                1250                1255                1260

Asp Arg Phe Ser Gly Arg Ile Ala Pro Ala Ala Gln Ser Ala Ser
    1265                1270                1275

Ser Ser His Arg Pro Ala Ser Gln Glu Gly Arg Ser Gly Asn Lys
    1280                1285                1290

Ser Tyr Ser Glu Glu Glu Leu Arg Glu Lys Ser Ile Ala Thr Ile
    1295                1300                1305

Arg Glu Tyr Tyr Ser Ala Lys Asp Glu Lys Glu Val Ala Leu Cys
    1310                1315                1320

Ile Glu Glu Leu Asn Ala Pro Ser Phe Tyr Pro Ser Leu Val Ser
    1325                1330                1335

Leu Trp Val Asn Asp Ser Phe Glu Arg Lys Asp Met Glu Arg Glu
    1340                1345                1350

Leu Leu Ala Lys Leu Phe Val Gly Leu Tyr Asn Gly Gly Tyr Asn
    1355                1360                1365

Leu Leu Ser Lys Pro Gln Leu Ile Glu Gly Leu Ser Ser Val Leu
    1370                1375                1380

Ala Ser Leu Glu Asp Ala Leu Ser Asp Ser Pro Arg Ala Ala Glu
    1385                1390                1395

Tyr Leu Gly Arg Leu Leu Ala Arg Phe Val Val Glu Lys Ile Leu
    1400                1405                1410

Val Leu Gln Asp Val Gly Lys Leu Ile Glu Glu Gly Gly Glu Glu
    1415                1420                1425

Pro Gly His Leu Val Gln Glu Gly Ile Ala Ala Asp Val Leu Gly
    1430                1435                1440

Ala Val Leu Glu Trp Ile Arg Thr Glu Lys Gly Asp Ser Phe Leu
    1445                1450                1455

Lys Glu Ala Lys Thr Ser Ser Asn Leu Lys Leu Glu Asp Phe Arg
    1460                1465                1470

Pro Gln His Leu Lys Arg Ser Lys Leu Asp Ala Phe Met Leu Thr
    1475                1480                1485

<210> SEQ ID NO 5
<211> LENGTH: 28
<212> TYPE: DNA
<213> ORGANISM: Artificial Sequence
<220> FEATURE:
<223> OTHER INFORMATION: Primer used to amplify a fragment of
      eIF(iso)4E-2

<400> SEQUENCE: 5
cacccgcaaa tggaggcaaa tggactgt                                      28

<210> SEQ ID NO 6
<211> LENGTH: 24
<212> TYPE: DNA
<213> ORGANISM: Artificial Sequence
<220> FEATURE:
<223> OTHER INFORMATION: Primer used to amplify a fragment of
      eIF(iso)4E-2

<400> SEQUENCE: 6
tccacctctg cttggtttct gact                                          24

<210> SEQ ID NO 7
<211> LENGTH: 28
<212> TYPE: DNA
<213> ORGANISM: Artificial Sequence
<220> FEATURE:
```

-continued

```
<223> OTHER INFORMATION: primer used to amplify a fragment of eIF4G

<400> SEQUENCE: 7
cacctcagca gcaccattgg tatctcca                                  28

<210> SEQ ID NO 8
<211> LENGTH: 23
<212> TYPE: DNA
<213> ORGANISM: Artificial Sequence
<220> FEATURE:
<223> OTHER INFORMATION: primer used to amplify a fragment of eIF4G

<400> SEQUENCE: 8
gctcggagca ttcaactcct caa                                       23
```

PLANT GERMPLASM RESISTANT TO RNA VIRUSES

CROSS-REFERENCE TO RELATED APPLICATION

This present application is a divisional application of U.S. application Ser. No. 14/494,661, filed Sep. 24, 2014, which itself claims priority under 35 U.S.C. § 119(e) to U.S. Provisional Ser. No. 61/882,116, which was filed on Sep. 25, 2013, the entirety of which is hereby incorporated by reference.

FIELD OF THE INVENTION

The present invention is related to silencing specific eukaryotic translation initiation factors in plants to produce a plant resistant to viruses such as Potyviruses, Luteoviruses, and Furoviruses. More specifically, the plant would be resistant to viruses such as Wheat streak mosaic virus, *Triticum* mosaic virus, Soil bourne mosaic virus, or Barley yellow dwarf virus.

BACKGROUND OF INVENTION

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) discloses a method to inhibit expression of a target gene in a cell, the method comprising introduction of a double stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separately complementary strands that hybridize to each other to form the said double-stranded construct, and the double-stranded construct inhibits expression of the target gene.

To utilize RNA interference as a method to regulate gene expression for control, a specific essential gene needs to be targeted. Coordinated gene expression requires factors involved in transcription and translation. Translation initiation coordinates activities of several eukaryotic initiation factors (eIF) or proteins which are classically defined by their cytoplasmic location and ability to regulate the initiation phase of protein synthesis. One of these factors, the eIF4F complex involves the expression of two proteins EIF(iso)4E-2 and EIF4G.

Disclosed in Caranta et al. (U.S. Pat. No. 7,919,677) is a method to obtain Potyvirus resistant plants having mutations in an eIF4E translation factor region. Additionally, disclosed in Jahn et al. (U.S. Pat. No. 7,772,462) is silencing of translation initiation factor eIF4E from *Capsicum annuum* imparted virus resistance to transgenic plants. Given the interest and showing of viral resistance to poyviruses related to eIF4 region, there is a need in the art to determine whether targeting eIF(iso)4E-2 or eIF4G via RNA interference induces viral resistance in vial susceptible plants.

BRIEF DESCRIPTION OF THE DRAWINGS

The present invention together with the above and other objects and advantages may best be understood from the following detailed description of the embodiment of the invention illustrated in the drawings, wherein:

FIG. 1A and FIG. 1B depicts a vector map for a CP fragment cloned into pANDA mini vector by means of homologous recombination via LR clonase.

BRIEF DESCRIPTION OF THE SEQUENCES

The invention can be more fully understood from the following detailed description and the accompanying sequence descriptions, which form a part of this application.

```
SEQ. ID. NO: 1:
ATGGCAGAGGTCGAAGCTGCGCTCCCGGTGGCGGCGACAGAGACCCCGGA

GGTCGCCGCCGAGGGCGACGCGGGTGCGGCCGAGGCGAAGGGGCCGCACA

AGCTGCAGCGGCAGTGGACCTTCTGGTACGACATCCAGACCAAGCCCAAG

CCCGGCGCCGCCTGGGGCACCTCGCTCAAAAAGGGCTACACCTTCGACAC

CGTCGAAGAGTTCTGGTGCTTGTATGATCAGATTTTCCGTCCGAGTAAGC

TGGTAGGAAGTGCTGATTTTCATTTATTCAAGGCTGGGGTAGAACCAAAG

TGGGAAGATCCAGAGTGCGCAAATGGAGGCAAATGGACTGTGATATCTAG

CAGGAAGACCAATCTTGATACCATGTGGCTTGAAACGTGTATGGCTCTGA

TTGGAGAGCAGTTCGATGAAAGCCAGGAAATTTGTGGTGTTGTTGCTAGT

GTCCGCCAGAGACAGGATAAGCTTTCATTATGGACTAAGACTGCCAGTAA

CGAAGCTGTTCAGGTGGACATTGGCAAGAAATGGAAGGAGGTTATTGACT

ACAATGATAAGATGGTCTACAGCTTCCACGATGACTCAAGAAGTCAGAAA

CCAAGCAGAGGTGGACGATACACCGTCTAA corresponds to the cDNA of eIF(iso)4E-2.

SEQ. ID. NO: 2:
MAEVEAALPVAATETPEVAAEGDAGAAEAKGPHKLQRQWTFWYDIQTKPK

PGAAWGTSLKKGYTFDTVEEFWCLYDQIFRPSKLVGSADFHLFKAGVEPK

WEDPECANGGKWTVISSRKTNLDTMWLETCMALIGEQFDESQEICGVVAS

VRQRQDKLSLWTKTASNEAVQVDIGKKWKEVIDYNDKMVYSFHDDSRSQK

PSRGGRYTV corresponds to the amino acid sequence encoded by SEQ. ID. NO: 1.

SEQ. ID. NO: 3:
ATGGGGCATCAAGGACAAACCATGATGTATCCGTCTGTTGCTCATCCAAT

CCCTCCTCAACTGGGCAATGTTAATTTGAACATGGCTTCACAGTATCCTC

AGCAACAGCAGAATAAGCTTGTTGCTCCTCGAAAGAGCAGTAATATCAAA

ATTACTGATCCAAACACTAACAAAGAAGTGGTTCTTGGGCGGCCTTCACC

TAATGTAGCAGTACAACCGCAGCAAGTCAGTGGTGTTGCAACTCAGCCTA

TGGTTTACTATACTAATCCACAGCAGACCTCGTATAACCAGTCAGGCACG

TATTACTCCGGCACTGCTGGTGTTGTTCCCACTGGATCACAGGGCAGGTT

TGGTTATCCTGCCACTCAAGCTGGTCAATCAATTCCTTTCATGAACCCTT

CTATGTCAAATACTGTTCCTGCCAGCCACAAGGACAACATAGCTGGGCCT
```

-continued

```
GCACCATCTGGTCAGTCCCAACTCATAGGCAAACCACAAGGTGGGTTGCA
CATGGAGAAACCTGTTCCCTCGGTCAAGATAAGTATGCCTGCAGGTAGAT
CAGACGCTTCTAAATTCGGGTCGCTGACCATGCGGTACAACATCGACAAA
AGGATAATGAAGTTATTTCTGGTGCTATGGTTTCGAATAAACCAGTTAGT
GAGAAGGAGAGCAAGGCACCATCTATCCCAGAGAAGCACTCCAAGGAAAG
TAAAGCACCATCTGCCGTGGAAGCATCCCACTGCGGTGACTCAACCTT
TACCGATTCAAGCTGCAAAGCCAGAAACTGATGCAGCGACTGCAAATTCA
CCCTCATTCTTGACCGGAGCTGATGAAAAGAAAGAATCCCTTCCAATGAC
TGATTCACTTAAGGATAACAAGAAAAATGCAACTAGAAATGACACAAAGA
ATTTGCCGCAACAACCTCAGTCTGCTTCCCCTGCCGAAGAGTTGAAGGGG
CAAACTTCTGTGAAGCTTGGTGATGATGTGGTTGGTCACATGGAAACCAA
GAGCTTCGATAGTGAAAAGGTGGATTTAACCAGCAAGGTTTCAGGCTTAA
CATCAGCAACATCTGAAAGTAGTATTTCTCCTATTCTTGGTAAAAGTGAA
GCTGACAGCACATCAGTAGATGCTGCTGATGTTCCTGCCATGGTAATCAG
CTCTGCAAAATTGTCCTCTGCGAGCACTGGGGAGCCCCAAGCAGTAGAAA
GCTTAGGTGTTGCTGCTGTTAAATCTAAGGAGATTGAAATAACTCACCAA
ATTTCACCTGAATCTAGTGATGGCAAAATTATGTCTGATTCTACTGAAAA
TGAATCACATGACTTCACGGTGGACTTGGCTGAGCAGGCATCATTGGCAA
CTTCAAAGCCTGGTAATTCAGATGCAACATCTTTTGTAACTGACCCGCAA
GAGCTACCCAAGGAGTGCACAACATCTGTACCGGAGGACCACAGTTTGAT
GAATACATCACATAATAAGGATACCCAAACTTTATCAGCTTCTGTGGATG
CCAGCGATGTGTCTGAGGTCAATTCTGGAACCTCATCAGAGTCTACCAGC
CAAAGTACCAACGATAAAGATATCAGAAGTAGCATTCAGGAAACTGGATT
AGCTGTTTCTGGTATTACTCCTGGCATGTTGCCTGTGAATCATTCAGTTG
CATCTGAGGGGCAAGTCAAACATGCAGATGGAGCGAAGGATGAGTCTAGT
ACTGAGCAATCAAGTGCCGTACCAACAGGTTCTGTTAGACCCTTATCAAG
GGAAAAACCTACTGCAGAGCTTGCCCGAACAAAGTCTACAGCTGGGAGAA
AGAAGAAACGGAAGGAAATGCTTTCAAAAGCTGATGCTGCTGGGAGCTCA
GATCTGTACAATGCATACAAAGGACCACAAGAACAGTCTGAGAGTGTTGC
CACATCAGACGGTGCTGATAGTTCTTCAACAGTCGACGGGACACATGTGC
TGCCTGAGGAATCAGAAAGGGAGGTGATGTGTGAGGACGATGGAAAGAAA
AAAGTTGAGCCGGATGATTGGGAAGATGCAGCAGACATGTCTACTCCAAA
GCTGCAAAGTTCGGACTCTGGAAACCAGGCTAGTGCAGTTCAATTGCCAG
ATTCTGATATGACTGAAGCTAATGGCCGAAAGAAATATTCTCGTGATTTT
CTTCTAACTTTTGCACATCAGTATTCTAGTCTTCCTGTTGGCATCCGGAT
GGATACTGTCACTAGTACGCTATTCAAAGATTTGGCAGGAAAATCCTATG
TTATTGATCGGAACCTCACCCAAGTTCTGCAAGGGGATCTGATAGACCA
ACATCTCGCGGTGATCGCCGTGGTCCTGCTATGGATGATGATAAGTGGTT
AAAATCAGGTGTTCCTTACAGTCCTAACCGTGATGCCCACATGGACTTGA
CAAACGGCCCAGCAATTAATTACCGTGGCGGCCCAGGAGGCGCTCATGGT
GTTCTGAGGAATCCACGTGGTGCACTCCTTGTGGGACCACAATCCAATGC
TCCTCAAGTACCCCGCAGTGGCTCTGATGCAGATAGATGGCAGCAAAAGG
GTCTGATCCCATCTCCTGTTACACCCATGCAAGTAATGCACAAAGCCGAG
AAAAAGTATGTTGTCGGCAAAGTTTCTGATGAGGAGCAGGCAAAGCAGAG
GCAGCTGAAAGCCATTCTGAATAAACTGACCCCACAAAACTTTGACAAGC
TTTTTGAACAAGTGAAAGAGGTGAACATTGACAATGTATCAACTCTTACT
GGGGTGATTTCACAGATATTTGACAAAGCTTTGATGGAACCAACTTTCTG
TGAAATGTATGCCAACTTCTGTTCCCATTTGGCTGGTGCCCTGCCAGACT
TTAGTGAGGACAATGAAAAGATTACATTCAAGAGACTGCTATTGAACAAG
TGCCAAGAGGAGTTTGAGAGGGGAGAAAGAGAAGAAGCTGAAGCAGATAA
AACGGAGGAGGAAGGTGAGATTAAGCAAACGAAAGAGGAAAGGGAAGAAA
AGAGAGTTAAAGCTCGAAGGCGCATGCTGGGTAATATTAGATTGATTGGA
GAATTGTACAAAAAGAGGATGTTGACAGAGCGCATCATGCATGAATGCAT
CAAAAAATTGTTGGGAAATTATCAGAATCCAGATGAGGAGAACATTGAAG
CACTATGCAAATTGATGAGTACAATTGGAGAGATGATAGATCATCCCAAG
GCTAAGGAACATATGGATGCNTATTTTGATAGAATGCGCAACCTGTCGAC
CAGTCAACTGATATCTTCCCGTGTTAGATTCCTGCTCAGAGATTCAATCG
ATCTCAGGAAGAACAAATGGCAGCAAAGGCGTAAAGTGGATGGCCCCAAG
AAGATTGATGAGGTTCACAGGGATGCAGCTCAGGAAAGACATGCTCAATC
GAGTAGGTCTCGTGGTCCAGTCGTTAGTTCTCTTCCAAGAAGAGGGGCAC
CCTCTATGGATTACGGCTCCCGTGGCTCAGCAGCACCATTGGTATCTCCA
GGTCCTCAGCAACGAGGGCGTGGATTTGGTAATCAAGATATTCGGTATGA
GCAGGAAAGGCATCAGTTTGATAGAACTGTTCCCCTTCCCCAGCGTTCTG
TAAAGGACGAAGCTATCACTCTTGGACCACAAGGTGGCCTAGCTAGGGGT
ATGTCTTTAAGAGGGCAGCCACCGGTATCAAATTCTGAACTTCCTAGTGT
TGTTGACCAGCGCAGGATTGTATCTGGTCCTAATGGGTACAATTCTGTGC
CTTCAACAACAAGAGAAGACACTAGCTCTAGAATTCCAGATCGATTTTCT
GGGAGAATAGCACCTGCTGCACAATCTGCTAGTTCTTCACACAGACCTGC
CAGCCAGGAGGGTCGTTCAGGAAATAAATCATACTCTGAGGAGGAATTGA
GAGAGAAATCTATTGCAACCATCCGGGAATATTATAGTGCGAAAGATGAA
AAGGAAGTTGCATTGTGTATTGAGGAGTTGAATGCTCCGAGCTTCTATCC
TTCTCTTGTATCACTTTGGGTAAATGATTCCTTTGAGAGGAAAGATATGG
AAAGAGAGTTGTTGGCAAAGCTCTTTGTCGGGCTTTACAATGGTGGATAT
AATTTATTGAGCAAGCCTCAGCTCATTGAGGGGCTTTCATCCGTTCTTGC
TTCATTGGAGGATGCTCTAAGTGATTCTCCAAGAGCGGCAGAGTATCTTG
GACGTCTTCTTGCAAGGTTTGTGGTGGAGAAGATACTGGTTTTGCAAGAC
GTAGGTAAATTGATTGAAGAAGGCGGAGAGGAGCCTGGACACCTTGTGCA
GGAAGGCATCGCAGCTGATGTCCTTGGCGCAGTCTTGGAGTGGATCAGAA
CAGAAAAGGGGGATTCCTTCTTGAAGGAGGCCAAGACAAGCTCCAATCTC
AAGTTGGAGGATTTCAGACCGCAGCATCTTAAGAGGTCAAAGTTGGATGC
CTTCATGTTGACTTAA corresponds to the cDNA of eIF4G.
```

-continued

SEQ. ID. NO: 4:
MGHQGQTMMYPSVAHPIPPQLGNVNLNMASQYPQQQQNKLVAPRKSSNIK

ITDPNTNKEVVLGRPSPNVAVQPQQVSGVATQPMVYYTNPQQTSYNQSGT

YYSGTAGVVPTGSQGRFGYPATQAGQSIPFMNPSMSNTVPASHKDNIAGP

APSGQSQLIGKPQGGLHMEKPVPSVKISMPAGRSDASKFGVADHAVQHRQ

KDNEVISGAMVSNKPVSEKESKAPSIPEKHSKESKAPSAVEKHPTAVTQP

LPIQAAKPETDAATANSPSFLTGADEKKESLPMTDSLKDNKKNATRNDTK

NLPQQPQSASPAEELKGQTSVKLGDDVVGHMETKSFDSEKVDLTSKVSGL

TSATSESSISPILGKSEADSTSVDAADVPAMVISSAKLSSASTGEPQAVE

SLGVAAVKSKEIEITHQISPESSDGKIMSDSTENESHDFTVDLAEQASLA

TSKPGNSDATSFVTDPQELPKECTTSVPEDHSLMNTSHNKDTQTLSASVD

ASDVSEVNSGTSSESTSQSTNDKDIRSSIQETGLAVSGITPGMLPVNHSV

ASEGQVKHADGAKDESSTEQSSAVPTGSVRPLSREKPTAELARTKSTAGR

KKKRKEMLSKADAAGSSDLYNAYKGPQEQSESVATSDGADSSSTVDGTHV

LPEESEREVMCEDDGKKKVEPDDWEDAADMSTPKLQSSDSGNQASAVQLP

DSDMTEANGRKKYSRDFLLTFAHQYSSLPVGIRMDTVTSTLFKDLAGKSY

VIDREPHPSSARGSDRPTSRGDRRGPAMDDDKWLKSGVPYSPNRDAHMDL

TNGPAINYRGGPGGAHGVLRNPRGALLVGPQSNAPQVPRSGSDADRWQQK

GLIPSPVTPMQVMHKAEKKYVVGKVSDEEQAKQRQLKAILNKLTPQNFDK

LFEQVKEVNIDNVSTLTGVISQIFDKALMEPTFCEMYANFCSHLAGALPD

FSEDNEKITFKRLLLNKCQEEFERGEREEAEADKTEEEGEIKQTKEEREE

KRVKARRRMLGNIRLIGELYKKRMLTERIMHECIKKLLGNYQNPDEENIE

ALCKLMSTIGEMIDHPKAKEHMDAYFDRMRNLSTSQLISSRVRFLLRDSI

DLRKNKWQQRRKVDGPKKIDEVHRDAAQERHAQSSRSRGPVVSSLPRRGA

PSMDYGSRGSAAPLVSPGPQQRGRGFGNQDIRYEQERHQFDRTVPLPQRS

VKDEAITLGPQGGLARGMSLRGQPPVSNSELPSVVDQRRIVSGPNGYNSV

PSTTREDTSSR1PDRFSGRIAPAAQSASSSHRPASQEGRSGNKSYSEEEL

REKSIATIREYYSAKDEKEVALCIEELNAPSFYPSLVSLWVNDSFERKDM

ERELLAKLFVGLYNGGYNLLSKPQLIEGLSSVLASLEDALSDSPRAAEYL

GRLLARFVVEKILVLQDVGKLIEEGGEEPGHLVQEGIAADVLGAVLEWIR

TEKGDSFLKEAKTSSNLKLEDFRPQHLKRSKLDAFMLT corresponds to the amino acid sequence encoded by

SEQ ID NO: 3.

SEQ. ID. NO: 5:
CACCCGCAAATGGAGGCAAATGGACTGT is a forward primer
used to amplify a fragment of eIF(iso)4E-2.

SEQ. ID. NO: 6:
TCCACCTCTGCTTGGTTTCTGACT is a reverse primer used
to amplify a fragment of eIF(iso)4E-2.

SEQ. ID. NO: 7:
CACCTCAGCAGCACCATTGGTATCTCCA is a forward primer
used to amplify a fragment of eIF4G.

SEQ. ID. NO: 8
GCTCGGAGCATTCAACTCCTCAA is a reverse primer used
to amplify a fragment of eIF4G.

DETAILED DESCRIPTION OF THE INVENTION

Disclosed herein is a method of producing a plant germplasm having resistance to RNA viruses, the method comprises introducing into a parental plant germplasm a chimeric DNA molecule comprising (i) a plant expressible promoter, (ii) a region which encodes dsRNA for eIF(iso)4E-2 or eIF4G which is capable of inhibiting RNA viral replication (iii) plant translation termination signal, b) transforming said parental plant germplasm, c) generating a plant germplasm from the parental plant germplasm comprising the chimeric DNA molecule; and d) selecting plant germplasm obtained from step (c) and identifying germplasm having immunity to viral RNA replication. In one embodiment of the invention, also disclosed is a transgenic plant produced by the method disclosed herein. In another embodiment of the invention, disclosed is a transgenic plant produced by the method disclosed where the plant is resistant to RNA plant viruses selected from the group consisting of Potyviruses, Luteoviruses, and Furoviruses. In yet another embodiment of the invention, disclosed is a transgenic plant produced by the method wherein the plant is resistant to Wheat streak mosaic virus. In yet another embodiment of the invention, disclosed is a transgenic plant produced by the method herein where the plant is resistant to *Triticum* mosaic virus. In yet another embodiment of the invention, disclosed is a transgenic plant produced by the method herein where the plant is resistant to Soil bourne mosaic virus. In another embodiment of the invention, disclosed is a transgenic plant produced by the method herein where the plant is resistant to Barley yellow dwarf virus.

In another embodiment of invention, the expression of transgenes and resistance phenotype remains stable in multiple generations of the progeny in the transgenic plant produced by the method herein. In another embodiment of the invention, the seed of a transgenic plant produced by the method herein.

In various embodiments of the invention, the method for transforming plant germplasm can be accomplish through a process selected from the group consisting of a biolistic particle delivery system, microprojectile bombardment, viral infection, *Agrobacterium*-mediated transformation, and electroporation.

In another embodiment of the invention, the method for producing a plant germplasm having resistance to RNA viruses is due to inhibited expression of an eIF(iso)4E-2 gene encoding a protein comprising SEQ. ID. NO: 2. In yet another embodiment of the invention, the method for producing a plant germplasm having resistance to RNA viruses is due to inhibited expression of an eIF4G gene encoding a protein comprising SEQ. ID. NO: 4. In another embodiment of the invention, disclosed is a transgenic plant having resistance to RNA viruses where said transgenic plant comprises a chimeric DNA molecule which encodes a double stranded RNA molecule for eIF(iso)4E-2 or eIF4G.

Disclosed herein is a nucleic acid construct comprising a nucleotide sequence of SEQ. ID. NO: 1 or an antisense sequence corresponding to SEQ. ID. NO: 1, wherein the construct is operably linked to a promoter that drives expression in a plant cell. Also disclosed is a vector comprising of the nucleic acid SEQ. ID. NO: 1. In an embodiment of the invention is a transgenic plant having stably incorporated in its genome the nucleotide sequence of SEQ. ID. NO:1.

Disclosed herein is a nucleic acid construct comprising of the nucleotide sequence of SEQ. ID. NO: 3 or an antisense sequence corresponding to SEQ. ID. NO: 3, wherein the construct is operably linked to a promoter that drives expression in a plant cell. Also disclosed is a vector comprising the nucleic acid SEQ. ID. NO: 3. In an embodiment of the invention is a transgenic plant having stably incorporated in its genome the nucleotide sequence of SEQ. ID. NO:3.

Disclosed herein is a non-transgenic plant comprising an eIF(iso)4E-2 allele in its genome, whereby the eIF(iso)4E-2 allele is an allele which encodes a protein comprising the amino acid sequence of SEQ. ID. NO: 1, characterized in that said eIF(iso)4E-2 allele comprises one or more mutations in its nucleotide sequence and whereby as a result of said one or more mutations the plant comprising said mutant allele in its genome has significant resistance to RNA viruses compared to a plant comprising a wild type eIF(iso)4E-2 allele in its genome. In an embodiment of the invention, disclosed is a non-transgenic plant produced by the method disclosed where the plant is resistant to RNA plant viruses selected from the group consisting of Potyviruses, Luteoviruses, and Furoviruses. In yet another embodiment of the invention, disclosed is a non-transgenic plant produced by the method wherein the plant is resistant to Wheat streak mosaic virus. In yet another embodiment of the invention, disclosed is a non-transgenic plant produced by the method herein where the plant is resistant to *Triticum* mosaic virus. In yet another embodiment of the invention, disclosed is a non-transgenic plant produced by the method herein where the plant is resistant to Soil bourne mosaic virus. In another embodiment of the invention, disclosed is a non-transgenic plant produced by the method herein where the plant is resistant to Barley yellow dwarf virus. In another embodiment of the invention, the seed of a non-transgenic plant produced by the method herein.

Disclosed is a non-transgenic plant comprising of an eIF4G allele in its genome, whereby the eIF4G allele is an allele which encodes a protein comprising the amino acid sequence of SEQ. ID. NO: 4, characterized in that said eIF4G allele comprises one or more mutations in its nucleotide sequence and whereby as a result of said one or more mutations the plant comprising said mutant allele in its genome has significant resistance to RNA viruses compared to a plant comprising a wild type eIF4G allele in its genome.

Definitions

To assist in the understanding of the invention, the following terms, as used herein, are defined below.

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences. In one embodiment of the invention, the gene target is eIF(iso)4E-2 and eIF4G.

As used herein, the term "isolated" includes a material removed from its original environment, e.g., the natural environment if it is naturally occurring. For example, a naturally occurring polypeptide present in a living organism is not isolated, but the same polynucleotide or polypeptide, separated from some or all of the coexisting materials in the natural system, is isolated. Such polypeptide can be expressed by a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g, *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)).

Methods commonly employed to determine identity between sequences include, for example, those disclosed in Carillo, H., and Lipman, D., *SIAM J. Applied Math.* (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The protein EIF(iso)4E-2 is also identified as eukaryotic translation initiation factor 4E-2, eIF-4E-2, eIF4E-2, eIF-(iso)4F, and eIF-(iso)4F p28 subunit.

The protein EIF4G is also identified as eukaryotic translation initiation factor 4G.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, the term "recombinant DNA construct" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

A nucleic acid sequence can be inserted into a vector by a variety of procedures. In general, the sequence is ligated to the desired position in a vector following digestion of the insert and the vector with appropriate restriction endonucleases. Alternatively, blunt ends in both the insert and the vector may be ligated. A variety of cloning techniques are known in the art, e.g., as described in Sambrook, J. et al., *Molecular Cloning, A Laboratory Manual*, Cold Spring Harbor Press, Plainview, N.Y, (1989) and Ausubel, F. M. et al., Current Protocols in Molecular Biology, John Wiley & Sons, New York, N.Y. (1989). Such procedures and others are deemed to be within the scope of those skilled in the art.

The vector can be in the form of a plasmid, a viral particle, or a phage. Preferably, as disclosed herein the vector is a bacterial vector. Other vectors include chromosomal, non-chromosomal and synthetic DNA sequences, pET-30a and derivatives of pET-30; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook, T. et al., *Molecular Cloning: A Laboratory Manual*, Cold Spring Harbor Press, Plainview, N.Y, (1989).

"Small interfering RNA" or "siRNA" refers to a short double-strand of ribonucleic acid, approximately 18 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

As used herein, "knock-down" is defined as the act of binding an oligonucleotide with a complementary nucleotide sequence of a gene as such that the expression of the gene or mRNA transcript decreases. In an embodiment, knock-down of a eIF(iso)4E-2 and eIF4G gene in a transgenic plant confers resistance against viral RNA for said transgenic plant.

dsRNA containing a nucleotide sequence complementary to a portion of the eukaryotic translation initiation factor gene, preferably eIF(iso)4E-2 and eIF4G. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for plant resistance to RNA viruses. Thus, sequence identity may be optimized by sequence comparison and alignment algorithms known in the art. Thus, the determination of percent identity between any two sequences can be accomplished using a mathematical algorithm. Non-limiting examples of such mathematical algorithms are the algorithm of Myers and Miller (1988. CABIOS 4: 11-17), the local homology algorithm of Smith et al. (1981. Adv. Appl. Math. 2: 482); the homology alignment algorithm of Needleman and Wunsch (1970. J. Mol. Biol. 48: 443-453); the search-for-similarity-method of Pearson and Lipman (1988. Proc. Natl. Acad. Sci. 85: 2444-2448; the algorithm of Karlin and Altschul (1990. Proc. Natl. Acad. Sci. USA 87: 2264), modified as in Karlin and Altschul (1993. Proc. Natl. Acad. Sci. USA 90: 5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA), MacVector and Assembler Version 12.7 (Macvector. 1939 High House Road, Cary, N.C. USA 27519. Alignments using these programs can be performed using the default parameters.

Greater than 90% sequence identity, or even 100% sequence identity, between the inhibitory RNA and the portion of the eukaryotic translation initiation factor target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 18, 19, 21, 25, 50, 100, 200, 300, 400, 491, 500, or 510 bases. In a preferred embodiment, the length of the constructed double-stranded nucleotide sequence is approximately from about 18 to about 510 nucleotides in length.

The dsRNA construct disclosed herein may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Expression of higher doses of double-stranded construct may yield more effective RNA viral plant resistance.

While the examples provided wherein describe dsRNA constructs targeting eukaryotic initiation factor genes eIF (iso)4E-2 and eIF4G, (GenBank Accession Nos. Q03389 and EF190330), it is contemplated that when read in conjunction with the teaching disclosed herein, the construction of other dsRNA constructs targeting other eukaryotic initiation factor complex members which in turn reduce or eliminate viral reproduction and replication are disclosed herein.

Additionally it is contemplated that the disclosure herein would teach the transfer of a nucleic acid fragment into the genome of a host organism, resulting in genetically stable inheritance, particularly in a plant. Host organisms containing the transformed nucleic acid fragments are referred to as "transgenic" organisms. Examples of methods of plant transformation include *Agrobacterium*-mediated transformation (De Blaere et al. 1987. Meth. Enzymol. 143: 277) and biolistic particle delivery or "gene gun" transformation technology (Klein et al. 1987. Nature (London) 327: 70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transformation of plant cells or for the establishment of transgenic plants have been described in, e.g., Pouwels et al. 1985. Supp. 1987. Cloning Vectors: A Laboratory Manual; Weissbach and Weissbach. 1989. Methods for Plant Molecular Biology, Academic Press, New York; and Flevin et al. 1990. Plant Molecular Biology Manual, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The teachings disclosed herein also teach generating a non-transgenic wheat plant having the genes for eIF(iso) 4E-2 or eIF4G silenced through the use of chemical mutagens such as ethyl methanesulfonate (EMS), radiation based mutagenesis such as fast neutron, or site directed mutagenesis, and targeted editing such as zinc finger nucleases, TALEN, or CRISPR technologies. An example would be to expose wheat seeds to 0.6% EMS. M0 seeds would be grown to maturity and allowed to self pollinate. Plants would be screened at the M2 generation for mutations in the eIF(iso)4E-2. DNA from lines would be pooled and TILLING would be used to identify mutant lines. Lines would be screened for resistance to WSMV and TriMV. Resistant lines would be used as germplasm for crop improvement. A second approach would be to use targeted mutations to alter the binding site of an initiation factor that binds to a binding protein to prevent interactions with viral proteins, thus preventing virus replication.

In an embodiment of the invention, targeted cleavage events can be used, for example, to induce targeted mutagenesis, induce targeted deletions of cellular DNA sequences, and facilitate targeted recombination and integration at a predetermined chromosomal ppTAC or ppeTAC locus. Techniques of nucleotide editing can be found for example, Urnov et al. (2010) Nature 435(7042):646-51; United States Patent Publications 20030232410; 20050208489; 20050026157; 20050064474; 20060188987; 20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) Proc. Natl. Acad, Sci. USA 104(9): 3055-3060 describes using designed ZFNs for targeted gene addition at a specified locus. U.S. Patent Publication 20110041195 describes methods of making homozygous diploid organisms.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

Example 1: Cloning of eIF(iso)4E-2 (SEQ. ID. NO: 2)

A search term of "eIF4F" was used to identify a partial cDNA sequence from the TIGR wheat EST database (http:\jcvi.org\wheat\ wheat gene index term TC383303). That sequence was used in a BLASTX search to find the full length *Triticum aestivum* L. EIF(iso)4E-2 amino acid sequence in GenBank (Accession number Q03389). The nucleotide sequence of Q03389 was used to design the primers used to clone a portion of eIF(iso)4E-2. Forward CACCCGCAAATGGAGGCAAATGGACTGT (SEQ. ID. NO: 5) and Reverse TCCACCTCTGCTTGGTTTCTGACT (SEQ. ID. NO: 6) primers were used to amplify a 298 fragment of eIF(iso)4E-2 from cDNA from the cultivar Bobwhite corresponding to nucleotides 318-615.

Figure 1B:
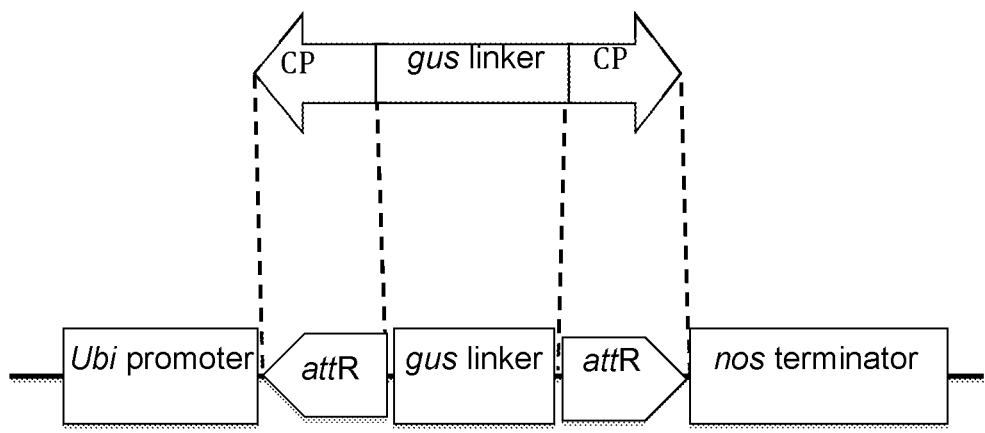

CACC was added to the 5' end of the forward primer for directional cloning of the PCR fragment into the entry vector pENTER-D/TOPO (Life Technologies) which carries two recombination sites, attL1 and attL2. The CP fragment was independently cloned into pANDA mini vector (Miki and Shimamoto, 2003; FIG. 1A, FIG. 1B) by means of homologous recombination via LR clonase (Invitrogen, Carlsbad, Calif.).

Example 2: Generation of Silenced eIF(iso)4E-2 Transgenic Wheat Conferring Resistance to Viruses The construct was bombarded in five independent biolistic experiments using approximately 900 independent wheat embryos. Embryogenic calli was transferred into glufosinate selection and regeneration cycles, where morphological differentiation occurred normally. One hundred and nineteen plants were generated under glufosinate selection, and transferred to soil. Plants were tested for glufosinate resistance and 15 herbicide resistant plants were identified. PCR analyses of these plants identified three with the hairpin construct. Lines were self fertilized and tested in the T3 generation. The majority of the lines derived from single seed descent that contained the gene of interest (GOI) and were expressing were resistant to Wheat streak mosaic virus (WSMV) and *Triticum* Mosaic Virus (TriMV) both individually and during co-infection (Table 1). Seed from the T2 generation were bulked for testing with Soilbourne mosaic virus (SbWMV). Soil infected with SbWMV was collected and used to grow plants. Most plants that had the GOI and were expressing the GOI were found to be resistant to the virus (Table 2). Bulked T2 seed was also used for testing resistance to Barley yellow dwarf virus (BYDV). A viruliferous aphid colony containing three strains of BYDV, -SGV, -MAV and PAV were used. Ten viruliferous aphids were placed individually on each plant and allowed time to infect. Aphids were then destroyed. Plants were allowed to recover. Most plants that contained the GOI and were expressing were found to be resistant (Table 3).

TABLE 1

Transgenic wheat plant expressing silenced eIF(iso)4E-2 co-infected with WSMV and TriMV. Transgenic plants were T3 generation derived by single seed selection. Transgenic Bobwhite controls were lines expressing only the bar gene for biolophos resistance.

| T3 eIF4(iso)4E-2 | Total Plants | GOI + and Expressing | Resistant to WSMV | Resistant to TriMV |
|---|---|---|---|---|
| 1550A | 50 | 47 | 45 | 45 |
| 1822A | 53 | 45 | 40 | 40 |
| 1814A | 54 | 52 | 43 | 43 |
| Transgenic Bobwhite w/o GOI | 24 | 0 | 0 | 0 |

TABLE 2

Transgenic wheat plant expressing silenced eIF(iso)4E-2 infected with SbWMV. Transgenic plants were T3 generation bulk derived T2 progeny. Transgenic Bobwhite controls were lines expressing only the bar gene for biolophos resistance.

| T3 eIF4(iso)4E-2 | Total Plants | GOI + and Expressing | Resistant to SbWMV |
|---|---|---|---|
| 1550A | 75 | 32 | 26 |
| 1822A | 70 | 28 | 24 |
| 1814A | 73 | 30 | 24 |
| Transgenic Bobwhite w/o GOI | 17 | 0 | 0 |

TABLE 3

Transgenic wheat plant expressing silenced eIF(iso)4E-2 infected with BYDV. Transgenic plants were T3 generation bulk derived T2 progeny. Transgenic Bobwhite controls were lines expressing only the bar gene for biolophos resistance.

| T3 eIF4(iso)4E-2 | Total Plants | GOI + and Expressing | Resistant to BYDV |
|---|---|---|---|
| 1550A | 16 | 3 | 3 |
| 1822A | 10 | 7 | 6 |
| 1814A | 9 | 6 | 6 |
| Transgenic Bobwhite w/o GOI | 2 | 0 | 0 |

Example 3: Cloning of eIF4G (SEQ: ID. NO. 4)

A search of "*Triticum aestivum* eIF4G" was used to identify the wheat eIF4G cDNA (EF190330) sequence from GenBank and used to design primers used to clone a portion of wheat eIF4G. The primers used were Forward CACCTCAGCAGCACCATTGGTATCTCCA (SEQ. ID. NO: 7) and Reverse GCTCGGAGCATTCAACTCCTCAA (SEQ. ID. NO: 8). The primers amplified a fragment of a 517 bp from regions 3479-3993 of the eIF4G sequence (EF190330). The fragment was amplified from cDNA from the cultivar Bobwhite.

CACC was added to the 5' end of the forward primer for directional cloning of the PCR fragment into the entry vector pENTER-D/TOPO (Life Technologies) which carries two recombination sites, attL1 and attL2. The CP fragment was independently cloned into pANDA mini vector (Miki and Shimamoto, 2003; FIG. 1A, 1B) by means of homologous recombination via LR clonase (Invitrogen, Carlsbad, Calif.).

Example 4: Generation of Silenced eIF4G Transgenic Wheat Conferring Resistance to Viruses A fragment of 517 bp from the host eukaryotic translation initiation factor G (GenBank Accession # EF190330.1) was cloned in pANDA mini and co-bombarded with pAHC20 in five independent biolistic experiments using approximately 900 wheat embryos. Embryogenic calli was transferred onto glufosinate selection. Seventy-two plants were generated under glufosinate selection and transferred to soil. PCR analyses confirmed the presence of the eIF4G hairpin construct in three lines of the bar-positive plants. Lines were self fertilized through the T3 generation. At the T3 generation, plants were inoculated with either WSMV or *Triticum mosaic virus* (TriMV) at the 2-3 leaf stage. Fourteen days later, plants were inoculated again to insure infection. Twenty-one days after the second inoculation, plants were scored for viral symptoms and compared to the nontransformed Bobwhite susceptible control. Leaf samples were also taken and used for ELISA to determine the presence of viral antigen. The majority of the lines that contained the gene of interest (GOI) were resistant to WSMV and TriMV both individually and during co-infection (Table 4). Seed from the T2 generation were bulked for testing with Soilbourne mosaic virus (SbWMV). Soil infected with SbWMV was collected and used to grow plants. Most plants that had the GOI and were expressing the GOI were found to be resistant to the virus (Table 5). Bulked T2 seed was also used for testing resistance to Barley yellow dwarf virus (BYDV). A viruliferous aphid colony containing three strains of BYDV, -SGV, -MAV and PAV were used. Ten viruliferous aphids were placed individually on each plant and allowed time to infect. Aphids were then destroyed. Plants were allowed to recover. Most plants that contained the GOI and were expressing were found to be resistant (Table 6). These results indicate the eIF4G hairpin construct provides resistance to the two potyviruses, the luteovirus and the furovirus.

TABLE 4

Transgenic wheat plant expressing silenced eIF4G co-infected with WSMV and TriMV. Transgenic plants were T3 generation derived by single seed selection. Transgenic Bobwhite controls were lines expressing only the bar gene for biolophos resistance.

| T3 eIF4G | Total Plants | GOI + and Expressing | Resistant to WSMV | Resistant to TriMV |
| --- | --- | --- | --- | --- |
| 1673A | 50 | 47 | 47 | 47 |
| 1742A | 51 | 48 | 48 | 48 |
| 1755A | 50 | 48 | 48 | 48 |
| 1830A | 46 | 52 | 42 | 42 |
| Transgenic Bobwhite w/o GOI | 24 | 0 | 0 | 0 |

TABLE 5

Transgenic wheat plant expressing silenced eIF4G infected with SbWMV. Transgenic plants were T3 generation bulk derived T2 progeny. Transgenic Bobwhite controls were lines expressing only the bar gene for biolophos resistance.

| T3 eIF4G | Total Plants | GOI + and Expressing | Resistant to SbWMV |
| --- | --- | --- | --- |
| 1673A | 10 | 6 | 6 |
| 1742A | 29 | 19 | 15 |
| 1755A | 20 | 12 | 9 |
| 1830A | 12 | 7 | 7 |
| Transgenic Bobwhite w/o GOI | 11 | 0 | 0 |

TABLE 6

Transgenic wheat plant expressing silenced eIF4G infected with BYDV. Transgenic plants were T3 generation bulk derived T2 progeny. Transgenic Bobwhite controls were lines expressing only the bar gene for biolophos resistance.

| T3 eIF4G | Total Plants | GOI + and Expressing | Resistant to BYDV |
| --- | --- | --- | --- |
| 1673A | 10 | 4 | 3 |
| 1742A | 5 | 1 | 1 |
| 1755A | 7 | 2 | 2 |
| 1830A | 5 | 3 | 3 |
| Transgenic Bobwhite w/o GOI | 7 | 0 | 0 |

While the invention has been described with reference to details of the illustrated embodiment, these details are not intended to limit the scope of the invention as defined in the appended claims. All cited references and published patent applications cited in this application are incorporated herein by reference. The embodiment of the invention in which exclusive property or privilege is claimed is defined as follows:

The invention claimed is:

1. A method of producing a plant germplasm having resistance to RNA viruses, the method comprising:

a) introducing into a parental plant germplasm a chimeric DNA molecule comprising (i) a plant expressible promoter, (ii) a region which encodes dsRNA for eIF4G which is capable of inhibiting RNA viral replication, and (iii) a plant translation termination signal, b) transforming said parental plant germplasm, c) generating a plant germplasm from the parental plant germplasm comprising the chimeric DNA molecule; and d) selecting plant germplasm obtained from step (c) and identifying germplasm having immunity to viral RNA replication, wherein the plant germplasm is a wheat plant germplasm, and wherein said resistance is due to inhibited expression of a eIF4G gene encoding a protein comprising SEQ. ID. NO: 4.

2. The plant germplasm produced by the method of claim 1.

3. The method of claim 1 wherein the plant is resistant to RNA plant viruses selected from the group consisting of Potyviruses, Luteoviruses, and Furoviruses.

4. The method of claim 1 wherein the plant is resistant to Wheat streak mosaic virus.

5. The method of claim 1 wherein the plant is resistant to *Triticum* mosaic virus.

6. The method of claim 1 wherein the plant is resistant to Soil bourne mosaic virus.

7. The method of claim 1 wherein the plant is resistant to Barley yellow dwarf virus.

8. The method of claim 1 wherein the expression of transgenes and resistance phenotype remains stable in multiple generations of the progeny.

9. The seed of a transgenic plant produced by the method of claim 1, wherein the seed has immunity to viral RNA replication, and wherein the seed comprises said chimeric DNA molecule.

10. The method of claim 1 wherein said transforming is through a process selected from the group consisting of a biolistic particle delivery system, microprojectile bombardment, viral infection, *Agrobacterium*-mediated transformation, and electroporation.

11. A transgenic wheat plant having resistance to RNA viruses, the transgenic plant comprising a chimeric DNA molecule which encodes a double stranded RNA molecule for eIF4G, wherein the transgenic plant is resistant to RNA viruses, and wherein said resistance is due to inhibited expression of a eIF4G gene encoding a protein comprising SEQ. ID. NO: 4.

12. A transgenic wheat plant comprising a nucleotide sequence that encodes a sequence encoding the polynucleotide sequence of SEQ. ID. NO: 3 or the antisense sequence corresponding to SEQ. ID. NO: 3, wherein said transgenic plant has increased resistance to positive strand RNA viruses.

* * * * *